United States Patent
Schlesinger et al.

[19]

[11] Patent Number: 6,149,599
[45] Date of Patent: Nov. 21, 2000

[54] METHOD FOR MANUFACTURING AN END PORTION SURROUNDING A CATHETER-MOUNTED PHASED-ARRAY ULTRASOUND TRANSDUCER

[75] Inventors: Randall L. Schlesinger, San Mateo, Calif.; Michael G. Curley, Cambridge, Mass.; John W. Eaton, Palo Alto, Calif.

[73] Assignee: Acuson Corporation, Mountain View, Calif.

[21] Appl. No.: 09/206,680

[22] Filed: Dec. 7, 1998

Related U.S. Application Data

[63] Continuation-in-part of application No. 08/791,598, Jan. 31, 1997, Pat. No. 5,846,205.

[51] Int. Cl.[7] .................................................. A61B 8/00
[52] U.S. Cl. ........................................... 600/472; 600/437
[58] Field of Search ........................... 604/488; 128/675; 600/437, 438, 472

[56] References Cited

U.S. PATENT DOCUMENTS

| | | | |
|---|---|---|---|
| 4,191,193 | 3/1980 | Seo | 128/675 |
| 4,809,704 | 3/1989 | Sogawa et al. | 128/675 |
| 5,865,801 | 2/1999 | Houser | 604/96 |

*Primary Examiner*—Marvin M. Lateef
*Assistant Examiner*—Maulin Patel
*Attorney, Agent, or Firm*—Brinks Hofer Gilson & Lione

[57] ABSTRACT

The preferred embodiments include a method for manufacturing an end portion surrounding a catheter-mounted phased-array ultrasound transducer. The material used for the end portion can be altered to give the end portion focusing, defocusing, or non-focusing characteristics. In one preferred embodiment, a thermoplastic material is injection molded or insert molded around a phased-array ultrasound transducer carried at a distal end of a catheter. In another preferred embodiment, a thermoset material is used to form the end portion using a casting or transfer molding technique. In yet another preferred embodiment, the phased-array ultrasound transducer is placed into a pre-formed end portion. The pre-formed end portion can be adhesively-attached to the phased-array transducer and catheter. If the pre-formed end portion is made from a thermoplastic material, the end portion can be thermally melted to attach the end portion to the phased-array transducer and catheter.

35 Claims, 4 Drawing Sheets

METHOD FOR MANUFACTURING AN END PORTION SURROUNDING A CATHETER-MOUNTED PHASED-ARRAY ULTRASOUND TRANSDUCER

RELATED APPLICATIONS

This is a continuation-in-part of application Ser. No. 08/791,598, filed Jan. 31, 1997, now U.S. Pat. No. 5,846,205.

BACKGROUND

This invention relates to catheter-mounted ultrasonic transducers of the phased-array type, and in particular to a method for manufacturing an end portion surrounding a catheter-mounted phased-array ultrasound transducer.

Catheter-mounted ultrasonic transducers have in the past taken several forms, including (1) single-element transducer crystals that are pointed radially outward and rotated about the axis of the catheter, (2) radial array transducers, and (3) linear array transducers. Bom U.S. Pat. No. 3,938,502 discloses one catheter-mounted ultrasonic array which utilizes a radial array arranged circumferentially around the axis of the catheter. Proudian U.S. Pat. No. 4,917,097 describes a similar radial array (and alludes to other geometries) that require multiplexing of the ultrasound signals near the elements of the array. Seward et al. (Seward, J. B., D. L. Packer, R. C. Chan, M. G. Curley, A. J. Tajik (1996), "Ultrasound Cardioscopy: Embarking on a New Journey," *Mayo Clinic Proceedings,* 71(7)) have described a phased array transducer for insertion into the heart. Such an array has the advantage of increased power: as the transducer array is made longer, the number of elements can be increased, thereby increasing the total radiation area.

Conventional phased-array, linear ultrasonic transducers are typically constructed using a piezoelectric material such as PZT. The piezoelectric material is formed into individual elements, arranged side by side with the lengths of individual elements parallel to one another. PZT is typically built on a backing material that reflects most of the ultrasound energy generated by the PZT, and also tends to absorb energy that is coupled into it. The active surface of the PZT is covered with a second material, called the matching layer, that couples ultrasonic energy from the PZT into the tissue that the transducer is in contact with. The backing material and the matching layer are typically made of composite material such as epoxy loaded with a heavier material such as alumina. By adjusting the phase of waveforms applied to the PZT elements, ultrasonic energy can be focused and steered within a plane oriented parallel to the array and the catheter axis. The techniques for designing transducers and steering them are discussed in texts such as Kino (*Acoustic Waves,* Prentice Hall, Englewood Cliffs, 1987) and Wells (*Biomedical Ultrasonics,* Academic Press, London, 1977).

Figure 7:
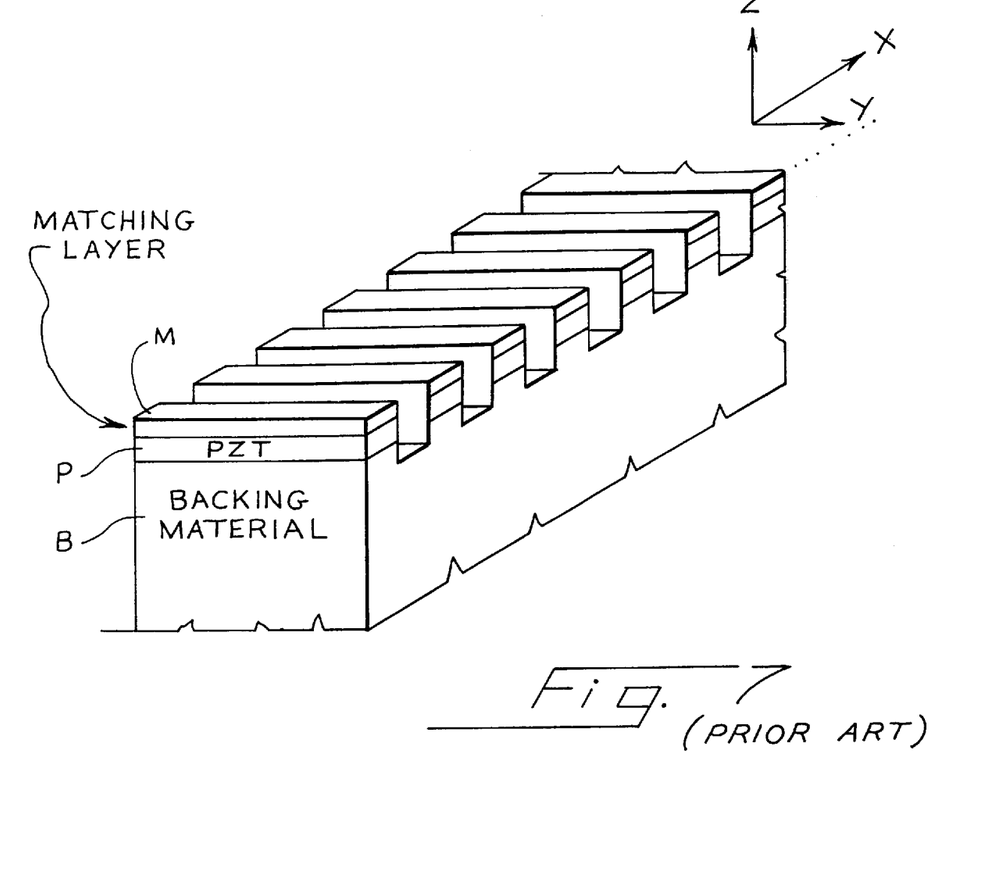
FIG. 7 is a schematic perspective view of a prior-art phased-array ultrasonic transducer.

FIG. 7 shows a prior-art, linear, phased-array transducer, and identifies the X, Y and Z coordinates for this transducer. In FIG. 7, the PZT material is identified by the reference symbol P, the backing material by the reference symbol B, and the matching layer by the reference symbol M. By properly controlling phase of the transducer signals applied to the individual piezoelectric elements P, the location and size of the focal spot in the XZ plane can be controlled. The size of the focal spot in the Y dimension is typically determined by a lens applied to the transducer. Such a lens focuses ultrasonic energy in the Y direction by taking advantage of the difference in the speed of sound in the lens material and in tissue in contact with the lens. If a lens has a speed of sound that is slower than that of adjacent tissue and is convex in shape, ultrasonic energy is caused to converge in the ZY plane. The ultrasonic energy focuses in a spot that is spaced from the piezoelectric elements P by a distance controlled by the radius of curvature of the lens and also by the difference in speed of sound between the lens and the adjacent tissue. As the speed of sound of the lens is made increasingly slower than that of adjacent tissue or as the radius of curvature of the lens is made progressively smaller, the focal spot approaches more closely to the transducer. When the focal spot is positioned close to the transducer, the width of the ultrasonic field rapidly diverges as the wave propagates past the focal spot. Of course, if the speed of sound in the lens is faster than in the adjacent tissue, the lens material would be formed in a concave shape to obtain the desired focusing.

It is desirable to maintain the width of the ultrasound field as thin as possible in the Y dimension. This keeps the intensity of the ultrasound energy as high as possible, which increases the strength of the reflected signal when the ultrasound is reflected by structures in the tissue. It is also desirable to keep the thickness of the field in the Y dimension as uniform as possible as the ultrasound propagates in the Z direction. This is because reflections of ultrasound energy at any particular depth that are detected at the transducer represent the integrated reflected energy within the ultrasound wave at that depth. If the ultrasound field is too wide, an object causing a reflection may be indistinguishable from the surrounding tissue. If the thickness of the ultrasound field varies from thin to thick as it propagates in Z, then an object that might be detected where the field is thin might not be detected where the field is wide, which is confusing and counterintuitive to the physician. Thus, it is desirable to maintain a thin, but uniform, ultrasound field width in the Y dimension as the wave propagates in the Z dimension.

Seward, et al. (Seward, J. B., D. L. Packer, R. C. Chan, M. G. Curley, A. J. Tajik (1996), "Ultrasound Cardioscopy: Embarking on a New Journey," *Mayo Clinic Proceedings,* 71(7)) have described a phased array ultrasound transducer for insertion into the heart. This transducer utilizes a linear phased array of the type shown in FIG. 7, and it offers many improvements over catheter-based radial imaging transducers of the past. These advantages are detailed in the Seward paper, but can be briefly listed as follows: the image plane is advantageous when imaging therapeutic interventions in the heart; the overall aperture of the transducer is large, improving the ultrasound energy and the penetration depth of the tissue; and the transducer is compatible with modern ultrasonic scanning systems.

The Seward transducer is made of conventional materials, including an epoxy-based backing block and a silicone-based lens. The transducer is constructed of 128 elements operating at 5 or 7 MHz. The total array extends for 14 mm in the X direction and 3.3 mm in the Y direction. The backing block is 5 mm in depth or more. As such, the overall diameter of this catheter is 8 mm. If the lens were formed into a cylinder with an 8 mm diameter, it would cause the ultrasound focus to be too close to the transducer, and the ultrasound field would then begin to diverge quickly, causing a loss of image quality and a loss of sensitivity and penetration depth. For this reason, the lens of the Seward transducer is flattened in the region of the transducer, making the forming of the final catheter more difficult.

A need presently exists for a catheter mounted, linear, phased-array transducer that is more easily manufactured.

SUMMARY

The present invention is defined by the following claims, and nothing in this section should be taken as a limitation on those claims.

By way of introduction, the preferred embodiments described below include a method for manufacturing an end portion surrounding a catheter-mounted phased-array ultrasound transducer. The material used for the end portion can be altered to give the end portion focusing, defocusing, or non-focusing characteristics. In one preferred embodiment, a thermoplastic material is injection molded or insert molded around a phased-array ultrasound transducer carried at a distal end of a catheter. In another preferred embodiment, a thermoset material is used to form the end portion using a casting or transfer molding technique. In yet another preferred embodiment, the phased-array ultrasound transducer is placed into a pre-formed end portion. The pre-formed end portion can be adhesively-attached to the phased-array transducer and catheter. If the pre-formed end portion is made from a thermoplastic material, the end portion can be thermally melted to attach the end portion to the phased-array transducer and catheter.

The preferred embodiments will now be described with reference to the attached drawings.

DETAILED DESCRIPTION OF THE PRESENTLY PREFERRED EMBODIMENTS

Figure 1:
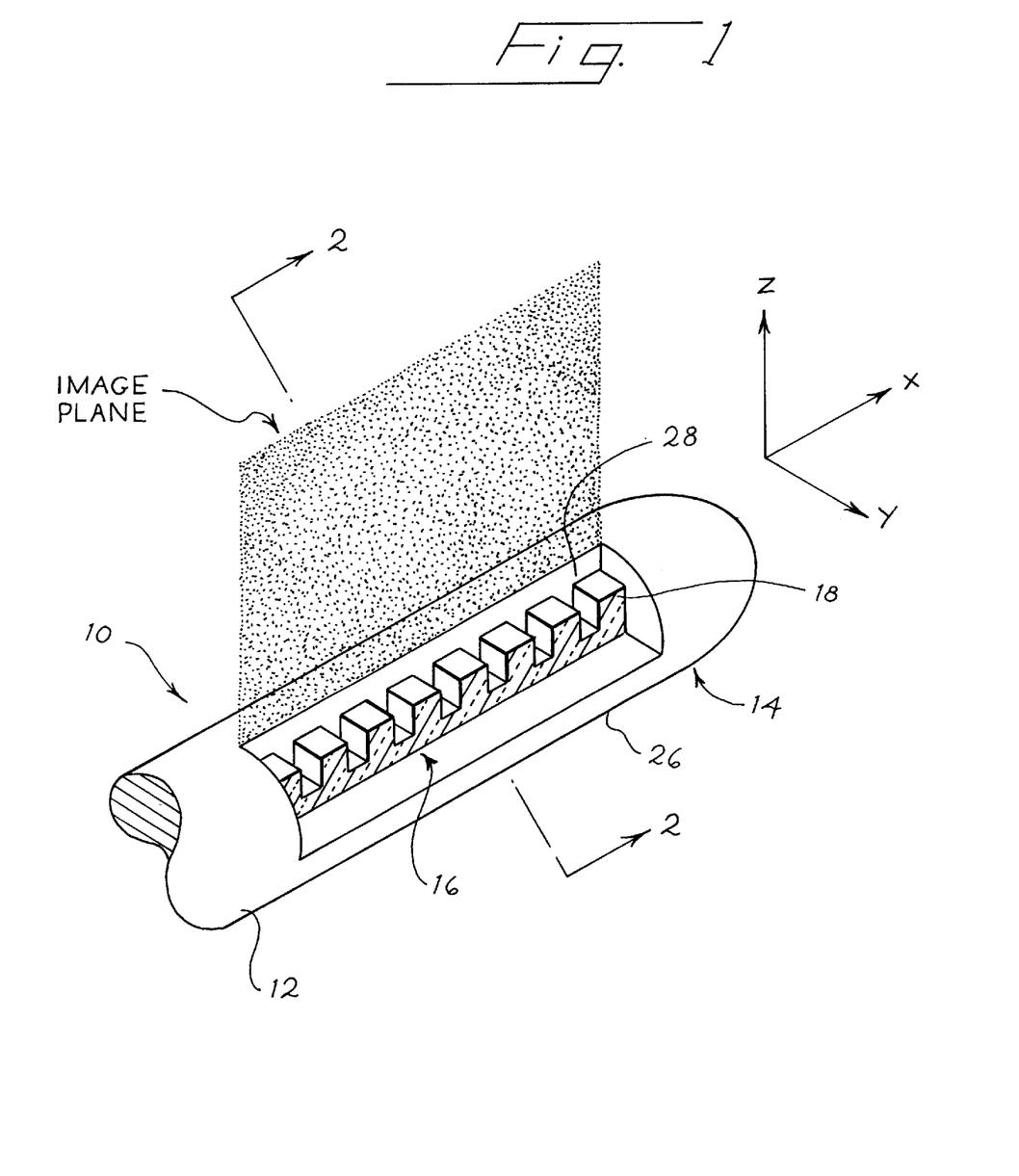
FIG. 1 is a perspective view in partial cutaway of a portion of a catheter-mounted transducer that incorporates a presently preferred embodiment of this invention.

Turning now to the drawings, FIG. 1 shows a perspective view of a transducer assembly 10 that incorporates a presently preferred embodiment of this invention. The transducer assembly 10 includes a catheter 12 which defines a distal end 14. In this embodiment the proximal end (not shown) is spaced from the distal end by about 110 centimeters, and the catheter 12 is circular in cross section and defines a maximum cross-sectional dimension of about 3.3 mm.

The distal end 14 of the catheter 12 carries a linear array 16 of transducer elements 18. The transducer elements 18 define an azimuthal axis which is denominated the X axis in FIG. 1, and is parallel to the longitudinal axis of the catheter 12.

Figures 2, 3:
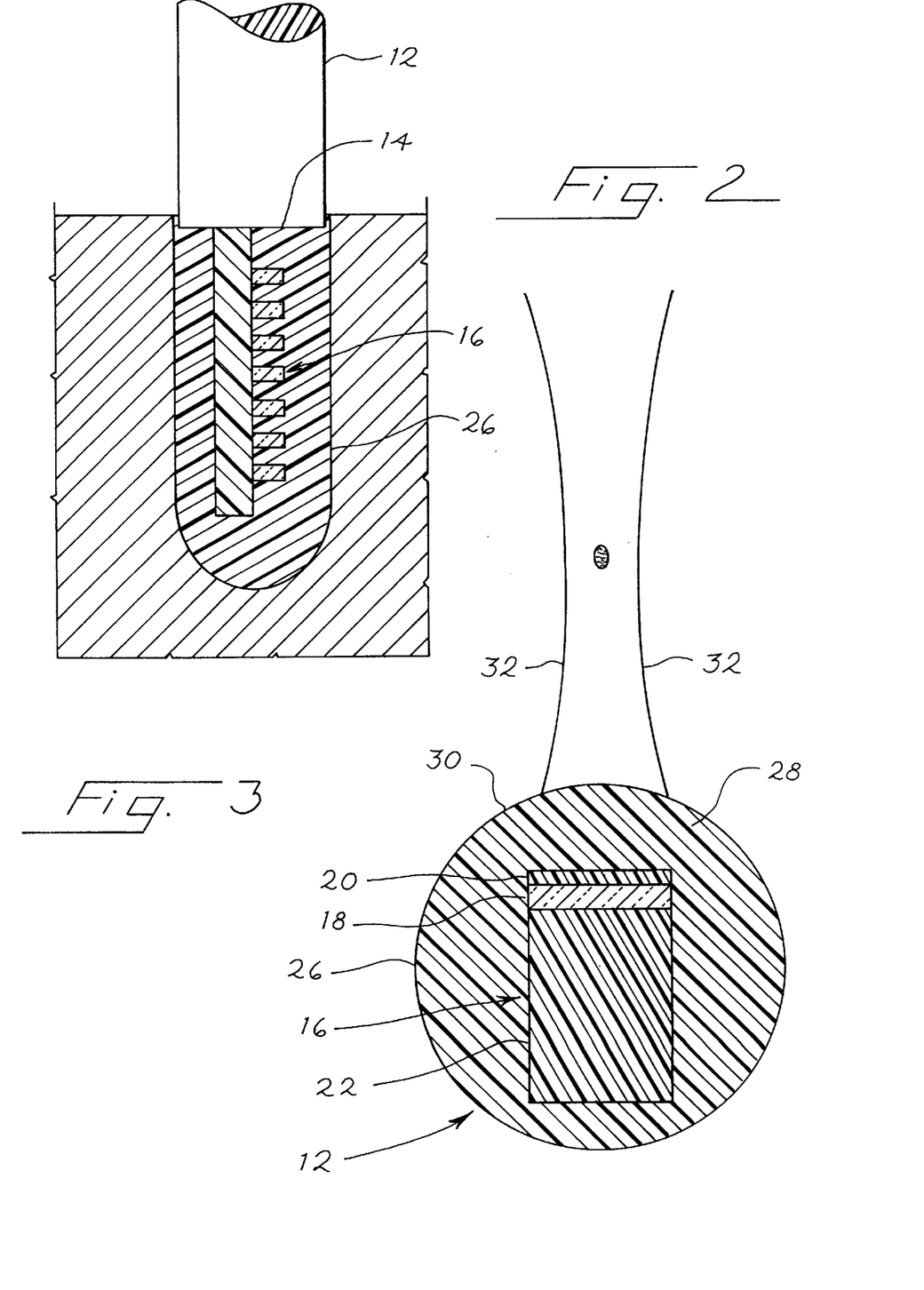
FIG. 2 is a cross-sectional view taken along line 2—2 of FIG. 1.
FIG. 3 is a partial sectional view showing the catheter of FIG. 1 at an intermediate stage of fabrication.

As shown in FIG. 2, the transducer array 16 includes a matching layer 20 adjacent the active surface of the transducer elements 18, and a backing layer 22 on the reverse side of the transducer elements 18. Flexible circuits are disposed in a lumen defined by the catheter 12 to carry transmit signals and receive signals between the individual transducer elements 18 and an ultrasonic diagnostic imaging system (not shown).

As shown in FIGS. 1 and 2, the catheter 12 includes an end portion 26 that is secured to the tube of the catheter 12 and surrounds the transducer array 16. The part of the end portion 26 that overlies the active surface of the transducer elements 18 forms an acoustic window 28. Typically, the end portion 26 and the acoustic window 28 may be formed of the same material, though this is not required. In this embodiment the end portion 26 is circular in cross section, and the radially outer surface 30 of the acoustic window 28 defines a radius of curvature which is substantially equal to one-half of the maximum cross-sectional dimension of the end portion 26. Since the end portion 26 is circular in cross section in this embodiment, the radius of curvature of the surface 30 is equal to the radius of curvature of the remaining parts of the end portion 26. This arrangement simplifies fabrication of the transducer assembly 10, because it eliminates both the need for a complex shape for the window, and the need for accurate registration between the transducer and the window.

Preferably the maximum cross-sectional dimension of the end portion 26 and the catheter 12 is less than 8 mm. This dimension is more preferably less than 3.3 mm, and most preferably less than 2 mm.

According to this invention, the acoustic window 28 is formed of a material that propagates ultrasonic waves at a speed comparable to or greater than the speed at which such ultrasonic waves propagate in adjacent tissue such as blood. As is known in the art, the propagation speed of ultrasound energy in blood is about 1570 meters per second, and the acoustic window 28 is preferably formed of a material having a comparable speed of sound for ultrasonic energy. The speed of sound in the window 28 is preferably greater than about 1250 m/sec. (1570 m/sec-20%), more preferably greater than about 1410 m/sec (1570 m/sec-10%), and most preferably greater than or equal to about 1570 m/sec. As used herein, the term "acoustic window" is intended to encompass both non-focusing and de-focusing elements between the active surface of the array and the tissue being scanned.

When the acoustic window 28 provides a speed of sound comparable to that of adjacent tissue, the radius of curvature of the radially outer surface 30 will not affect the focusing characteristics of the transducer array 16. In contrast, if conventional materials were used for the acoustic window 28 and the radius of curvature of the radially outer surface 30 were maintained at 1.5 millimeters (3 mm diameter for the end portion 26), the result would be an ultrasonic focus located too close to the transducer array 16. Such a close focus would cause the ultrasonic field to diverge rapidly at depths greater than the focal region, causing poor image quality and a loss of imaging depth.

However, it may be desirable to increase the thickness in the Y dimension if the natural thickness when the field is unfocussed is too thin. If the field is too thin, then objects would appear, then disappear from the image if the catheter, hence the ultrasound field, were rotated slightly. If the speed of sound in the material surrounding the transducer were greater than in the surrounding blood, and this material were convex, then the ultrasound field would diverge upon exiting the catheter. This would increase the thickness of the field in the Y dimension, which would have desirable properties for keeping objects in the image field with slight rotation of the transducer.

The design of the ultrasound imaging field may be different for different applications. When the image field needs to be wide, then a material with a speed of sound faster than that of blood can be used. When it is desirable to keep the image width narrow, and with minimal variation in the thickness of the image field, then a material with a speed of sound close to that of blood can be used.

In FIG. 2, lines 32 schematically show the ultrasonic field boundaries for the situation where the acoustic window 28 is formed of a material having a speed of sound close to that of tissue. If this material also has an acoustic impedance close to that of tissue, the ultrasound field generated by the transducer array 16 propagates as if it is simply contacting the tissue, and there is no significant reflection of the ultrasonic field as it exits the acoustic window 28. Similarly, there is no significant reflection of ultrasonic energy at this interface because of the substantially identical acoustic impedance on both sides of the surface 30.

Preferably, the length of each transducer element 18 in the Y direction is larger than a wavelength of ultrasonic energy, and the material of the acoustic window 28 is selected as described above. In this case the transducer array 16 will exhibit a gentle, natural focus. The distance in the Z dimension from the transducer array 16 to the location at which the thickness of the ultrasonic field in the Y dimension is smallest is approximately equal to $$\text{FocalDepth} = \frac{l^2 f}{2c},$$

where c is the speed of sound in tissue (1570 m/sec), l is the elevational length of the transducer elements 18, and f is the ultrasound frequency. When the transducer 16 measures 2.5 mm in the Y dimension and operates at 7 MHz in a 3.3 mm diameter catheter having an acoustic window as described above, the point of best focus is approximately 14 mm away from the transducer array 16. Beyond this depth the ultrasound field gradually diverges in the Y dimension.

The use of non-focusing material for the acoustic window 28 both improves the imaging characteristics of the transducer array 16 and simplifies manufacture of the acoustic window 28. In particular, the acoustic window 28 can be formed with a simple cylindrical shape, and in this way the need for compound curvatures in the region of the transducer is completely avoided, along with the need for precise registration between the transducer and the compound curvatures.

The end portion can be manufactured with a thermoplastic (preferably Pebax) or a thermoset (preferably urethane) polymer. A thermoplastic material is a polymer that softens and is moldable when heated, hardens when cooled, and softens with subsequent heatings. A thermoset material is a polymer that polymerizes upon heating but does not soften upon subsequent heating. The properties of the polymer (whether thermoplastic or thermoset) can be altered to obtain focusing, defocusing, and non-focusing characteristics of the end portion.

FIG. 3 illustrates one method of fabricating the end portion 26 of the transducer assembly 10. According to this method, a transducer array 16 as described above is connected to the distal end 14 of a conventional catheter 12. The transducer array 16 is placed within a cavity of a cylindrical mold, which may for example be formed of anodized aluminum and provided with a nickel/Teflon coating, covered with a silicone-based mold release. It is preferred that the catheter 12 be inserted deeply enough into the mold to ensure that the end portion will surround the array 16 and adhere to the distal end 14 of the catheter 12. The mold release material ensures that the end portion will easily release from the mold after forming.

When a thermoplastic material is used, the mold can be used to create the end portion using injection molding or insert molding. With injection molding, the distal portion of the catheter with the phased array transducer is positioned into the cavity of the mold, and the mold halves clamp on one end around the catheter body. Molten thermoplastic material is injected into the cavity and adheres to the transducer and catheter main body. If the thermoplastic material is similar to the catheter body, a thermally fused joint may be achieved. After the thermoplastic material is injected, the mold is cooled, and the thermoplastic material solidifies. The solidified end portion is then ejected from the mold along with attached catheter. Insert molding is similar to injection molding except for the use of inserts (such as pins) to locate the transducer in the mold. As the molten thermoplastic material is injected into the mold and the thermoplastic material starts to solidify, the pins can be retracted, and advancing material can be used to fill the voids left by the pins. Alternatively, the end portion can be solidified with the pins in place. After the end portion is ejected, the voids left by the pins can be either reflowed away by localized melting or filled with an alternate material.

When a thermoset material is used, the mold can be used to create the end portion using a casting or transfer molding technique. Using the casting technique, the distal portion of the catheter with the phased array transducer is positioned into the cavity of the mold, and the mold halves clamp on one end around the catheter body. A thermoset material can be premixed using a liquid resin and hardener. In the liquid partially cured state, the thermoset material is pumped into the cavity to form the end portion around the transducer and to form the distal tip of the catheter. The liquid material cures to a solidified state either at room temperature or at an elevated temperature. The solidified end portion can be ejected from the mold along with the attached catheter. Chemical bonding takes place between the thermoset plastic, the transducer, and the main catheter body.

Transfer molding is similar to the casting technique except instead of using a liquid resin and hardener, the resin and hardener are mixed together in dry powder format and partial cured into a dry pellet. The distal portion of the catheter with the phased array transducer is positioned into the cavity of the mold, and the mold halves clamp on one end around the catheter body. The dry pellet is quickly heated to liquify the thermoset material, which is then injected into the cavity to form an end portion around the transducer and the distal tip of the catheter. The liquid material can cure to a solidified state either at room temperature or at an elevated temperature. The solidified end portion can be ejected from the mold along with attached catheter. Chemical bonding would take place between the thermoset plastic, the transducer, and the main catheter body.

Figures 4, 5:
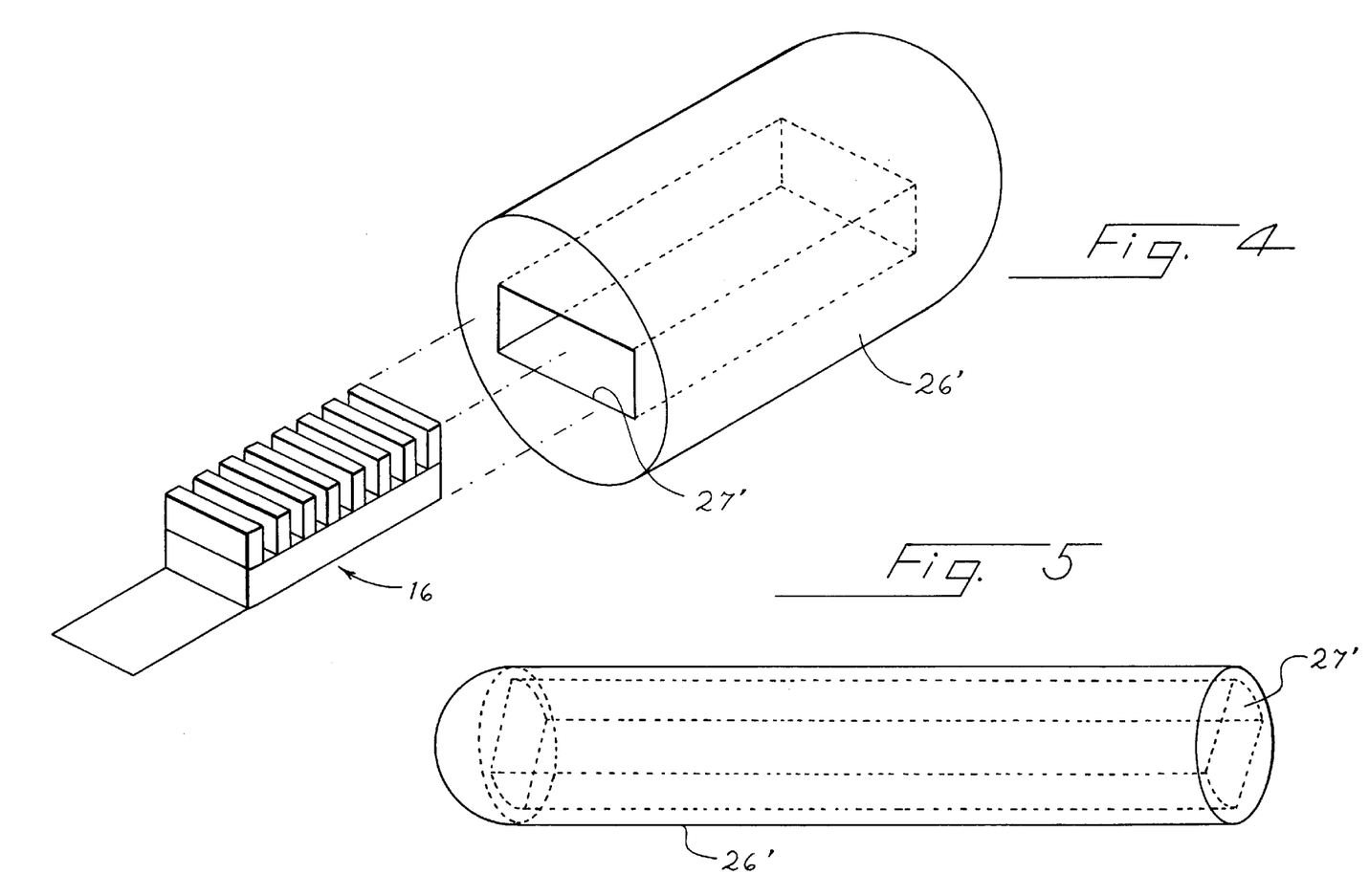
FIG. 4 is an exploded prospective view showing an alternate construction for the catheter of FIG. 1.
FIG. 5 is a perspective view of the end portion of FIG. 4.

One potential drawback of the method of FIG. 3 is that it requires precise placement of the array within the mold, and such placement can complicate fabrication. An alternative method, which avoids such placement difficulties, uses a pre-formed end portion 26'. The end portion 26' is preferably molded into the shape shown in FIG. 5. As shown in FIG. 5, the end portion 26' includes a longitudinally extending cavity 27'. The pre-formed end portion 26' has an outer shape in the desired final catheter geometry, and the inner cavity 27' is shaped to receive the array 16. Preferably, the inner cavity 27' conforms closely to the array 16 to eliminate pockets of air. This cavity 27' preferably has a flat surface adjacent the active surface of the array 16 and curved side surfaces that accommodate the electrical connections attached to the array 16. The cavity 27' is closed at the distal end, and the distal end of the end portion 26' is smoothly tapered to provide the desired end geometry for the catheter.

Figure 6:
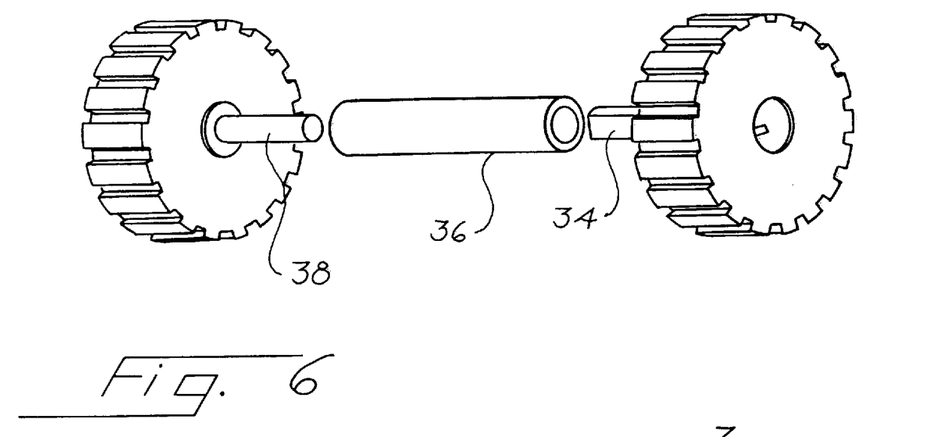
FIG. 6 is a schematic perspective view showing fixtures useful in assembling the embodiment of FIG. 4.

The end portion 26' is preferably molded into the shape shown in FIG. 5. As shown in FIG. 4, the pre-formed end portion 26' is pushed over the array 16. Assembly can be accomplished by inserting the assembly of the end portion 26' and the array 16 into a glass tube 36 having the proper inner diameter for the final assembly (FIG. 6). This tube can be for example approximately 1.5 inches in length. A die 38 having a concave recess shaped to correspond to the desired shape for the distal end of the end portion 26' is inserted into the glass tube 36. This die 38 is used to immobilize the end portion 26' and to apply pressure. A mandrel 34 is inserted into the opposite end of the glass tube 36 and is used to apply pressure opposing that of the die 38.

The pre-formed end portion 26' may be created with either a thermoplastic material or a thermoset material and can be created, for example, by injection molding or by using dies, glass tubing, a hot air source, and mandrels with the proper shapes for the desired outside dimensions and inner cavity. When a thermoplastic material is used, the end portion can be reheated to reflow the thermoplastic to thermally bond to the transducer and catheter main body. If the material is similar to the catheter body, a thermally fused joint may be achieved. For example, using a heating device such as a hot air knife, the assembly can be heated, and pressure can be gently applied to the assembly by opposed forces on the mandrel 34 and the die 38. As the end portion 26' softens with heat, the pressure supplied by the die 38 and the mandrel 34 helps to eliminate any air gaps and to form and to bond the pre-formed end portion 26' to the array 16. The final assembly can then be cooled either by an air gun or otherwise, and the hardened, reflowed assembly can then be removed from the glass tubing 36. This method minimizes exposure of the array 16 to undesirably high temperatures.

Alternatively, when either a thermoplastic or thermoset material is used, before insertion of the transducer into the pre-formed element, an adhesive can be applied to the transducer or the pre-formed element to bond the two pieces together. The adhesive may require time to cure and may require an elevated temperature to cure. Chemical bonding can take place between the adhesive and the thermoset plastic, the transducer, and the main catheter body.

In order better to define the presently preferred embodiments of this invention, the following details of construction are provided. It should be understood that these details are intended only by way of example.

The backing layer 22 may be formed as described in Sliwa U.S. Pat. No. 5,297,553, assigned to the assignee of this invention. The backing material disclosed in the Sliwa patent provides excellent acoustic properties while allowing the matching layer 20 and therefore the catheter 12 to be provided with an extremely low profile. The end portion 26, 26' may be formed of urethane (for example the resin CY8721 sold by Ciba-Geigy) or polyether block Amides (for example the resin Pebax sold by Autochem). Urethane may be used as an adhesive to secure the Pebax end portion to the catheter.

Preferably, flexible circuits as described in U.S. Pat. No. 5,795,299, assigned to the assignee of the present invention, can be used in the catheter 12. If desired, the catheter 12 can be made disposable, and the inter connection system described in U.S. Pat. No. 5,797,848, also assigned to the assignee of the present invention, can be used. Each of these U.S. patents is hereby incorporated by reference.

From the foregoing, it should be apparent that an improved transducer assembly has been described that uses a non-focusing or defocusing material to form an acoustic window adjacent to the active surface of the transducer array. In this way the imaging characteristics of the catheter are improved, and manufacturing is simplified.

Of course, it should be understood that a wide range of changes and modifications can be made to the preferred embodiments described above. For example, the acoustic window may be formed of other materials having a speed of sound and acoustic impedance which match that of adjacent tissue. The diameter and length of the catheter and the end portion can all be adapted for the particular application, as can details of construction regarding the transducer array. If desired, the catheter can be provided with guidewire ports to allow the catheter to be inserted into the heart or blood vessels over a guidewire, or it can be provided with articulation wires to allow the catheter to be steered. Additionally, many other fabrication techniques can be used to fabricate the transducer assembly, and the broadest definitions of this invention are not intended to be limited to any particular fabrication technique.

It should therefore clearly be understood that the foregoing detailed description has discussed only a few of the many possible forms that the present invention can take. It is intended that only the following claims, including all equivalents, be regarded as a definition of this invention.

We claim:

1. A method for manufacturing an end portion surrounding a phased-array ultrasound transducer carried on a distal end of a catheter, the method comprising:
   (a) positioning a phased-array ultrasound transducer carried on a distal end of a catheter into a cavity of a mold;
   (b) introducing a polymer in a fluid form into the cavity, the polymer forming an end portion surrounding the phased-array ultrasound transducer when reaching in a hardened state; and
   (c) removing the phased-array ultrasound transducer from the cavity after the polymer reaches said hardened state.

2. The method of claim 1, wherein (b) comprises injecting a molten thermoplastic material into the cavity, and wherein (c) comprises removing the phased-array ultrasound transducer from the cavity after the molten thermoplastic material solidifies.

3. The method of claim 2, wherein the thermoplastic material comprises Pebax.

4. The method of claim 2, wherein (a) comprises positioning a phased-array ultrasound transducer carried on a distal end of a catheter into a cavity of a mold comprising at least one insert.

5. The method of claim 2 further comprising retracting said at least one insert when the molten thermoplastic material begins to solidify.

6. The method of claim 5, wherein said retracting creates at least one void, and wherein the method further comprises filling the at least one void with an advancing material.

7. The method of claim 4, wherein said at least one insert creates at least one void in the end portion, and wherein the method further comprises filling the at least one void after the end portion is removed from the cavity.

8. The method of claim 4, wherein said at least one insert creates at least one void in the end portion, and wherein the method further comprises melting a section of the end portion near the at least one void after the end portion is removed from the cavity.

9. The method of claim 1, wherein (b) comprises introducing a thermoset material in a fluid form into the cavity, the polymer forming an end portion surrounding the phased-array ultrasound transducer when the thermoset material cures into a solidified state, and wherein (c) comprises removing the phased-array ultrasound transducer from the cavity after the thermoset material cures into a solidified state.

10. The method of claim 9, wherein the thermoset material comprises urethane.

11. The method of claim 9, wherein the thermoset material comprises a liquid resin mixed with a hardener.

12. The method of claim 9 further comprising heating a dry resin/hardener pellet to form a thermoset material in a fluid form.

13. The method of claim 1, wherein (a) comprises positioning a phased-array ultrasound transducer carried on a distal end of a catheter into a cavity of a cylindrical mold characterized by a maximum cross-sectional dimension less than about 8 mm.

14. The method of claim 1, wherein (a) comprises positioning a phased-array ultrasound transducer carried on a distal end of a catheter into a cavity of a cylindrical mold characterized by a maximum cross-sectional dimension less than about 3.3 mm.

15. The method of claim 1, wherein (a) comprises positioning a phased-array ultrasound transducer carried on a distal end of a catheter into a cavity of a cylindrical mold characterized by a maximum cross-sectional dimension less than about 2 mm.

16. The method of claim 1, wherein (b) comprises introducing a polymer in a fluid form into the cavity, the polymer forming an end portion surrounding the phased-array ultrasound transducer when reaching in a hardened state, the end portion being substantially non-focusing to ultrasound waves.

17. The method of claim 1, wherein (b) comprises introducing a polymer in a fluid form into the cavity, the polymer forming an end portion surrounding the phased-array ultrasound transducer when reaching in a hardened state, the end portion operative to conduct ultrasound waves to and from an active surface of the phased-array ultrasound transducer with a speed of 1570 m/sec + or −20%.

18. The method of claim 1, wherein (b) comprises introducing a polymer in a fluid form into the cavity, the polymer forming an end portion surrounding the phased-array ultrasound transducer when reaching in a hardened state, the end portion operative to conduct ultrasound waves to and from an active surface of the phased-array ultrasound transducer with a speed of 1570 m/sec + or −10%.

19. The method of claim 1, wherein (b) comprises introducing a polymer in a fluid form into the cavity, the polymer forming an end portion surrounding the phased-array ultrasound transducer when reaching in a hardened state, the end portion operative to conduct ultrasound waves to and from an active surface of the phased-array ultrasound transducer with a speed of 1570 m/sec + or −5%.

20. The method of claim 1, wherein (b) comprises introducing a polymer in a fluid form into the cavity, the polymer forming an end portion surrounding the phased-array ultrasound transducer when reaching in a hardened state, the end portion operative to conduct ultrasound waves to and from an active surface of the phased-array ultrasound transducer with a speed of about 1570 m/sec.

21. A method for manufacturing an end portion surrounding a phased-array ultrasound transducer carried on a distal end of a catheter, the method comprising:
(a) pre-forming an end portion defining a longitudinally-extending cavity shaped to receive a phased-array ultrasound transducer carried on a distal end of a catheter; and
(b) inserting the phased-array ultrasound transducer into the longitudinally-extending cavity of the end portion.

22. The method of claim 21, further comprising applying an adhesive to the end portion before inserting the phased-array ultrasound transducer into the longitudinally-extending cavity of the end portion.

23. The method of claim 21, wherein (a) comprises pre-forming, with a thermoplastic material, an end portion defining a longitudinally-extending cavity shaped to receive a phased-array ultrasound transducer carried on a distal end of a catheter.

24. The method of claim 21, wherein the thermoplastic material comprises Pebax.

25. The method of claim 21 further comprising heating the end portion to thermally bond the end portion to the phased-array ultrasound transducer and catheter.

26. The method of claim 21, wherein (a) comprises pre-forming, with a thermoset material, an end portion defining a longitudinally-extending cavity shaped to receive a phased-array ultrasound transducer carried on a distal end of a catheter.

27. The method of claim 21, wherein the thermoset material comprises urethane.

28. The method of claim 21, wherein (a) comprises pre-forming an end portion defining a longitudinally-extending cavity shaped to receive a phased-array ultrasound transducer carried on a distal end of a catheter and having a maximum cross-sectional dimension less than about 8 mm.

29. The method of claim 21, wherein (a) comprises pre-forming an end portion defining a longitudinally-extending cavity shaped to receive a phased-array ultrasound transducer carried on a distal end of a catheter and having a maximum cross-sectional dimension less than about 3.3 mm.

30. The method of claim 21, wherein (a) comprises pre-forming an end portion defining a longitudinally-extending cavity shaped to receive a phased-array ultrasound transducer carried on a distal end of a catheter and having a maximum cross-sectional dimension less than about 2 mm.

31. The method of claim 21, wherein (a) comprises pre-forming an end portion defining a longitudinally-extending cavity shaped to receive a phased-array ultrasound transducer carried on a distal end of a catheter and being substantially non-focusing to ultrasound waves.

32. The method of claim 21, wherein (a) comprises pre-forming an end portion defining a longitudinally-extending cavity shaped to receive a phased-array ultrasound transducer carried on a distal end of a catheter and operative to conduct ultrasound waves to and from an active surface of the phased-array ultrasound transducer with a speed of 1570 m/sec + or −20%.

33. The method of claim 21, wherein (a) comprises pre-forming an end portion defining a longitudinally-extending cavity shaped to receive a phased-array ultrasound transducer carried on a distal end of a catheter and operative to conduct ultrasound waves to and from an active surface of the phased-array ultrasound transducer with a speed of 1570 m/sec + or −10%.

34. The method of claim 21, wherein (a) comprises pre-forming an end portion defining a longitudinally-extending cavity shaped to receive a phased-array ultrasound transducer carried on a distal end of a catheter and operative to conduct ultrasound waves to and from an active surface of the phased-array ultrasound transducer with a speed of 1570 m/sec + or −5%.

35. The method of claim 21, wherein (a) comprises pre-forming an end portion defining a longitudinally-extending cavity shaped to receive a phased-array ultrasound transducer carried on a distal end of a catheter and operative to conduct ultrasound waves to and from an active surface of the phased-array ultrasound transducer with a speed of about 1570 m/sec.

* * * * *

UNITED STATES PATENT AND TRADEMARK OFFICE
CERTIFICATE OF CORRECTION

PATENT NO.    : 6,149,599
DATED         : November 21, 2000
INVENTOR(S)   : Randall L. Schlesinger et al.

It is certified that error appears in the above-identified patent and that said Letters Patent is hereby corrected as shown below:

Title page,
Item [56], under U.S. PATENT DOCUMENTS, insert the following:
--    3,938,502    2/1976    Bom    --.
Under U.S. PATENT DOCUMENTS, insert the following:
--    4,605,009    8/1986    Pourcelot et al.
      4,794,931    1/1989    Yock    --.
Insert the following:
--    4,841,977    6/1989     Griffith et al.
      4,917,097    4/1990     Proudian, deceased et al.
      4,947,852    8/1990     Nassi et al.
      4,951,677    8/1990     Crowley et al.    --.
      5,078,148    1/1992     Nassi et al.
      5,240,003    8/1993     Lancee et al.
      5,284,148    2/1994     Dias et al.
      5,291,893    3/1994     Slayton
      5,297,553    3/1994     Sliwa, Jr. et al.
      5,305,756    4/1994     Entrekin et al.
      5,325,860    7/1994     Seward et al.
      5,336,182    8/1994     Lundquist et al.
      5,345,940    9/1994     Seward et al.
      5,364,352    11/1994    Cimino et al.
      5,368,037    11/1994    Eberle et al.
      5,368,558    11/1994    Nita
      5,375,602    12/1994    Lancee et al.
      5,389,096    2/1995     Alta et al.
      5,398,689    3/1995     Connor et al.
      5,417,219    5/1995     Takamizawa et al.
      5,400,785    3/1995     Crowley
      5,456,258    10/1995    Kondo et al.
      5,476,107    12/1995    Oakley et al.
      5,489,270    2/1996     Van Erp
      5,492,126    2/1996     Hennige et al.
      5,499,630    3/1996     Hiki et al.
      5,507,294    4/1996     Lum et al.
      5,509,418    4/1996     Lum et al.
      5,562,096    10/1996    Hossack et al.
      5,577,506    11/1996    Dias
      5,624,399    4/1997     Ackerman
      5,699,805    12/1997    Seward et al.
      5,704,361    1/1998     Seward et al.
      5,713,363    2/1998     Seward et al.

UNITED STATES PATENT AND TRADEMARK OFFICE
CERTIFICATE OF CORRECTION

PATENT NO.    : 6,149,599
DATED         : November 21, 2000
INVENTOR(S)   : Randall L. Schlesinger et al.

It is certified that error appears in the above-identified patent and that said Letters Patent is hereby corrected as shown below:

<u>Title page, (cont.)</u>
        5,722,402    3/1998    Swanson et al.
        5,722,403    3/1998    McGee et al.
        5,785,704    7/1998    Bille et al.    --.
Column 2, after line 2, insert the following:
        --OTHER PUBLICATIONS
Seward, J.B, D.L. Packer, R.C. Chan, M.G. Curley, A.J. Tajik, "Ultrasound Cardioscopy: Embarking on a New Journey," Mayo Clinic Proceedings, July 1996, 71 (7) : 629-635.

Wells, "Biomedical Ultrasonics," Academic Press, 1977, pp. 38-42. --.

<u>Column 3,</u>
Line 31, delete "prospective" and substitute -- perspective -- in its place.

<u>Column 4,</u>
Line 51, delete "unfocussed" and substittue -- unfocused -- in its place.

<u>Column 5,</u>
Line 24, delete "I" and substitute -- 1 -- ins its place.

<u>Column 7,</u>
Line 57, delete "inter connection" and subtitute -- inter-connection -- in its place.

Signed and Sealed this

Eighteenth Day of June, 2002

*Attest:*

JAMES E. ROGAN
*Attesting Officer*    *Director of the United States Patent and Trademark Office*